United States Patent
Yamashita et al.

(10) Patent No.: US 12,037,455 B2
(45) Date of Patent: Jul. 16, 2024

(54) RESIN COMPOSITION, MOLDED PRODUCT, METHOD FOR PRODUCING MOLDED PRODUCT, AND ANTIOXIDANT

(71) Applicant: Mitsubishi Gas Chemical Company, Inc., Tokyo (JP)

(72) Inventors: Momoko Yamashita, Hiratsuka (JP); Kazuya Sato, Hiratsuka (JP); Hatsuki Oguro, Hiratsuka (JP); Takafumi Oda, Hiratsuka (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 527 days.

(21) Appl. No.: 17/417,959

(22) PCT Filed: Nov. 29, 2019

(86) PCT No.: PCT/JP2019/046718
§ 371 (c)(1),
(2) Date: Jun. 24, 2021

(87) PCT Pub. No.: WO2020/137350
PCT Pub. Date: Jul. 2, 2020

(65) Prior Publication Data
US 2022/0073679 A1    Mar. 10, 2022

(30) Foreign Application Priority Data

Dec. 27, 2018  (JP) .................. 2018-244408

(51) Int. Cl.
  *C08G 69/28*    (2006.01)
  *C08K 5/17*    (2006.01)
  *C09K 15/18*    (2006.01)

(52) U.S. Cl.
  CPC ............... *C08G 69/28* (2013.01); *C08K 5/17* (2013.01); *C09K 15/18* (2013.01)

(58) Field of Classification Search
  CPC .................................. C09K 15/18; C08K 5/17
  See application file for complete search history.

(56) References Cited

U.S. PATENT DOCUMENTS

| | | |
|---|---|---|
| 2003/0235666 A1 | 12/2003 | Buhler |
| 2009/0306308 A1 | 12/2009 | Blondel et al. |
| 2010/0203275 A1 | 8/2010 | Hoffmann et al. |
| 2011/0111154 A1 | 5/2011 | Lêet al. |
| 2014/0134371 A1 | 5/2014 | Hoffmann et al. |
| 2016/0032051 A1 | 2/2016 | Kwon et al. |
| 2016/0280856 A1 | 9/2016 | Kanda et al. |
| 2017/0002144 A1 | 1/2017 | Kanda et al. |
| 2018/0171075 A1 | 6/2018 | Tsunaka et al. |

FOREIGN PATENT DOCUMENTS

| | | |
|---|---|---|
| CN | 1467236 A | 1/2004 |
| CN | 101421332 A | 4/2009 |
| CN | 101796099 A | 8/2010 |
| CN | 102066462 A | 5/2011 |
| CN | 105764956 A | 7/2016 |
| JP | 2004-083858 A | 3/2004 |
| JP | 2009-528399 A | 8/2009 |
| JP | 2010-534256 A | 11/2010 |
| JP | 2011-524928 A | 9/2011 |
| JP | 2015-105331 A | 6/2015 |
| WO | 2016/208272 A1 | 12/2016 |

OTHER PUBLICATIONS

Extended European Search Report issued in corresponding European Application No. 19904812.5 dated Feb. 7, 2022 (10 pages).
International Preliminary Report on Patentability and Written Opinion for PCT/JP2019/046718, dated Jan. 28, 2020, and English Translation submitted herewith (10 pages).
International Search Report for PCT/JP2019/046718, dated Jan. 28, 2020, and English Translation submitted herewith (6 pages).
Zhong, H. et al., "Study of 4,4'-methylenebis-cyclohexanamine as a high temperature-resistant shale inhibitor," Journal of Materials Science, 2016, vol. 51, No. 16, pp. 7585-7597.
Office Action issued in corresponding Chinese Application No. 201980085386.1 dated Oct. 9, 2021 (6 pages).

*Primary Examiner* — Wenwen Cai
(74) *Attorney, Agent, or Firm* — Fitch, Even, Tabin & Flannery LLP

(57) ABSTRACT

To provide a polyamide resin composition preventing mold fouling during molding and capable of producing a molded product with an excellent color tone, as well as a molded product, a method for producing a molded product, and an antioxidant. The composition is a resin composition containing: a polyamide resin constituted of diamine-derived constituent units and dicarboxylic acid-derived constituent units, 70 mol % or more of the diamine-derived constituent units being derived from a compound represented by Formula (1), and 70 mol % or more of the dicarboxylic acid-derived constituent units being derived from an α,ω-linear aliphatic dicarboxylic acid having from 8 to 12 carbon atoms; and a compound represented by Formula (1), where $R^1$ and $R^2$ each independently represent an alkyl group having from 1 to 4 carbon atoms, and n1 and n2 are each independently an integer from 0 to 4, wherein a content of the compound represented by Formula (1) is from 3 to 100 mass ppm of the resin composition.

Formula (1)

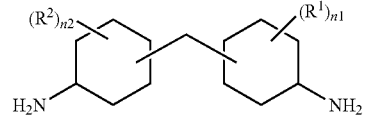

19 Claims, No Drawings

RESIN COMPOSITION, MOLDED PRODUCT, METHOD FOR PRODUCING MOLDED PRODUCT, AND ANTIOXIDANT

FIELD OF THE INVENTION

The present invention relates to a resin composition, a molded product, a method for producing a molded product, and an antioxidant.

BACKGROUND OF THE INVENTION

Of polyamide resins, crystalline resins have been widely used in the art, but in recent years, amorphous polyamide resins have been investigated because of their transparency and are used in wide variety of applications from industrial to highly designed applications, such as switch covers, lenses, and eye glass frames. For example, Patent Document 1 describes an amorphous polyamide resin.

CITATION LIST

Patent Documents

Patent Document 1: WO 2016/208272

SUMMARY OF INVENTION

However, the present inventors investigated and found that, for example, when an amorphous polyamide resin formed from a diamine, such as 4,4'-methylenebis(2-methylcyclohexane-1-amine) and 4,4'-methylenebis(cyclohexane-1-amine), and an aliphatic dicarboxylic acid is molded, a color tone (yellowness) may deteriorate. In addition, the present inventors found that fouling may occur in a mold or the like during injection molding. The present invention is to solve such problems, and an object of the present invention is to provide a polyamide resin composition with an excellent color tone and less likely to cause fouling in a mold or the like. Another object of the present invention is to provide a molded product formed from the polyamide resin composition, a method for producing a molded product, and an antioxidant.

As a result of diligent research conducted by the present inventor under the problems described above, the above problems have been solved by using a composition containing a specific amorphous polyamide resin and from 3 to 100 mass ppm of a diamine having a specific structure. Specifically, the above problems have been solved by the following means.

(1) A resin composition containing:
  a polyamide resin constituted of diamine-derived constituent units and dicarboxylic acid-derived constituent units,
  70 mol % or more of the diamine-derived constituent units being derived from a compound represented by Formula (1), and
  70 mol % or more of the dicarboxylic acid-derived constituent units being derived from an α,ω-linear aliphatic dicarboxylic acid having from 8 to 12 carbon atoms; and a compound represented by Formula (1):

Formula (1)

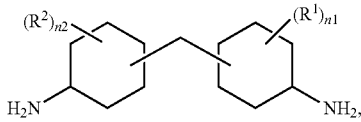
[Chem. 1]

where $R^1$ and $R^2$ each independently represent an alkyl group having from 1 to 4 carbon atoms, and n1 and n2 are each independently an integer of 0 to 4,
wherein a content of the compound represented by Formula (1) is from 3 to 100 mass ppm of the resin composition.

(2) The resin composition according to (1), wherein the compound represented by Formula (1) is represented by Formula (2):

Formula (2)

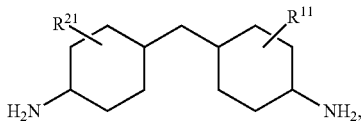
[Chem. 2]

where $R^{11}$ and $R^{21}$ each independently represent a hydrogen atom or an alkyl group having from 1 to 4 carbon atoms.

(3) The resin composition according to (1), wherein the compound represented by Formula (1) is at least one selected from the group consisting of 4,4'-methylenebis(2-methylcyclohexane-1-amine) and 4,4'-methylenebis(cyclohexane-1-amine).

(4) The resin composition according to any one of (1) to (3), wherein 70 mol % or more of the dicarboxylic acid-derived constituent units are a constituent unit(s) derived from at least one of sebacic acid and dodecanedioic acid.

(5) The resin composition according to any one of (1) to (4), wherein the polyamide resin is an amorphous polyamide resin.

(6) The resin composition according to any one of (1) to (5), wherein 95 mass % or more of the resin composition is the polyamide resin.

(7) The resin composition according to any one of (1) to (6), wherein the content of the compound represented by Formula (1) is from 18 to 70 mass ppm of the resin composition.

(8) A molded product formed from the resin composition described in any one of (1) to (7).

(9) A method for producing a molded product, the method including molding the resin composition described in any one of (1) to (7).

(10) An antioxidant for polyamide resins, the antioxidant containing a compound represented by Formula (1):

Formula (1)

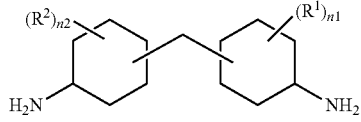
[Chem. 3]

where $R^1$ and $R^2$ each independently represent an alkyl group having from 1 to 4 carbon atoms, and n1 and n2 are each independently an integer from 0 to 4.

The present invention can provide a polyamide resin composition with an excellent color tone and less likely to cause fouling in a mold or the like during molding, as well as a molded product, a method for producing a molded product, and an antioxidant.

DESCRIPTION OF EMBODIMENTS

The contents of the present invention will be described in detail below. In the present specification, "from . . . to . . . " or "of . . . to . . . " is used to mean that the numerical values described before and after "to" are included as the lower limit and the upper limit, respectively.

A resin composition of the present invention is characterized in that a resin composition contains: a polyamide resin (which may be hereinafter referred to as the "specific polyamide resin") constituted of diamine-derived constituent units and dicarboxylic acid-derived constituent units, 70 mol % or more of the diamine-derived constituent units being derived from a compound represented by Formula (1), and 70 mol % or more of the dicarboxylic acid-derived constituent units being derived from an α,ω-linear aliphatic dicarboxylic acid having from 8 to 12 carbon atoms; and a compound represented by Formula (1):

Formula (1)

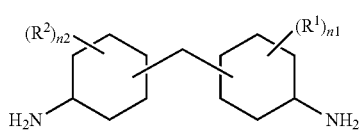

[Chem. 4]

where $R^1$ and $R^2$ each independently represent an alkyl group having from 1 to 4 carbon atoms, and n1 and n2 are each independently an integer from 0 to 4, and is characterized in that a content of the compound represented by Formula (1) is from 3 to 100 mass ppm of the resin composition.

Such a constitution provides a polyamide resin composition with an excellent color tone and less likely to cause fouling in a mold or the like when molded. The reason for this is speculative, but the compound represented by Formula (1) has a hindered amine structure, thus acts as an antioxidant and adjusts the color tone. That is, the constitution containing the compound represented by Formula (1) can improve the color tone. In particular, the compound represented by Formula (1) is a raw material monomer for the specific polyamide resin or a compound similar to the raw material monomer. Therefore, the compound has good compatibility with the specific polyamide resin and thus is preferred.

On the other hand, the compound represented by Formula (1) if contained in a large amount would volatilize during molding and, for example, when the resin composition is injection-molded, the compound would adhere to a mold when the mold is cooled. As a result, gas burning or the like may occur in a molded product. If gas burning occurs, the mold must be cleaned, thus reducing productivity. Thus, the amount of the compound represented by Formula (1) is reduced, and thus the volatilization as described above can be relatively prevented. Injection molding has been described as an example, but also in other molding methods (e.g., extrusion molding), adhesion of the compound represented by Formula (1) to a machine, apparatus, device, or the like used for molding is similarly observed.

The present invention will be described in detail below.

Polyamide Resin

The polyamide resin (specific polyamide resin) used in the present invention is constituted of diamine-derived constituent units and dicarboxylic acid-derived constituent units, in which 70 mol % or more of the diamine-derived constituent units are derived from a compound represented by Formula (1), and 70 mol % or more of the dicarboxylic acid-derived constituent units are derived from an α,ω-linear aliphatic dicarboxylic acid having from 8 to 12 carbon atoms. Such a polyamide resin is an amorphous polyamide resin and provides a molded product with excellent transparency.

Of the diamine-derived constituent units contained in the specific polyamide resin, 70 mol % or more of the diamine-derived constituent units are derived from a compound represented by Formula (1), preferably 75 mol % or more, more preferably 80 mol % or more, further more preferably 85 mol % or more, even more preferably 90 mol % or more, still more preferably 95 mol % or more, and yet even more preferably 99 mol % or more are derived from a compound represented by Formula (1).

Only one, or two or more types of diamine constituent units derived from a compound represented by Formula (1) may be used. When two or more types of diamine constituent units are used, the total amount is in the above range.

Formula (1)

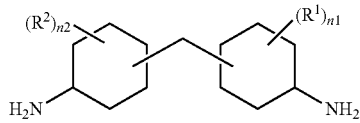

[Chem. 5]

where $R^1$ and $R^2$ each independently represent an alkyl group having from 1 to 4 carbon atoms, and n1 and n2 are each independently an integer from 0 to 4.

$R^1$ and $R^2$ are each independently preferably a methyl group, an ethyl group, or a propyl group, more preferably a methyl group or an ethyl group, and even more preferably a methyl group. $R^1$ and $R^2$ may be the same group or may be different but is preferably the same group.

n1 and n2 are each independently preferably an integer from 0 to 3, more preferably an integer from 0 to 2, and even more preferably an integer of 0 or 1.

The compound represented by Formula (1) is preferably a compound represented by Formula (2):

Formula (2)

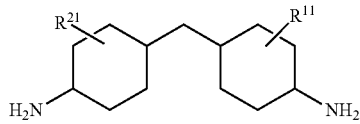

[Chem. 6]

where $R^{11}$ and $R^{21}$ each independently represent a hydrogen atom or an alkyl group having from 1 to 4 carbon atoms. When $R^{11}$ and $R^{21}$ are each independently an alkyl group having from 1 to 4 carbon atoms, $R^{11}$ and $R^{21}$ are each independently preferably a methyl group, an ethyl group, or a propyl group, more preferably a methyl group or an ethyl group, and even more preferably a methyl group. $R^{11}$ and $R^{21}$ are each independently preferably a hydrogen atom or a methyl group, and more preferably both $R^{11}$ and $R^{21}$ are hydrogen atoms or both are methyl groups.

The compound represented by Formula (1) is preferably a compound represented by Formula (3):

Formula (3)

[Chem. 7]

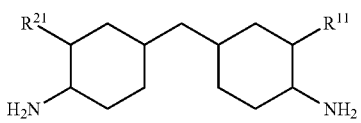

where $R^{11}$ and $R^{21}$ are synonymous with $R^{11}$ and $R^{21}$ in Formula (2), and the preferred ranges are also the same.

The compound represented by Formula (1) is preferably at least one selected from the group consisting of 4,4'-methylenebis(2-methylcyclohexane-1-amine) and 4,4'-methylenebis(cyclohexane-1-amine).

Among the diamines constituting the diamine constituent unit that can be contained in the specific polyamide resin, the diamine other than the compound represented by Formula (1) is exemplified by aliphatic diamines, alicyclic diamines, and aromatic diamines.

The aliphatic diamine is preferably an aliphatic diamine having from 6 to 12 carbon atoms, and examples include linear aliphatic diamines, such as 1,6-hexanediamine, 1,7-heptanediamine, 1,8-octanediamine, 1,9-nonanediamine, 1,10-decanediamine, 1,11-undecanediamine, and 1,12-dodecanediamine; and branched aliphatic diamines, such as 2-methyl-1,8-octanediamine, 4-methyl-1,8-octanediamine, 5-methyl-1,9-nonanediamine, 2,2,4-/2,4,4-trimethylhexamethylenediamine, 2-methyl-1,5-pentanediamine, 2-methyl-1,6-hexanediamine, and 2-methyl-1,7-heptanediamine.

The alicyclic diamine is exemplified by 1,2-bis(aminomethyl) cyclohexane, 1,3-bis(aminomethyl) cyclohexane, 1,4-bis(aminomethyl) cyclohexane, isophorone diamine, 4,4'-thiobis(cyclohexane-1-amine), and 4,4'-thiobis(cyclohexane-1-amine).

The aromatic diamine is exemplified by m-xylylenediamine and p-xylylenediamine.

Of the dicarboxylic acid-derived constituent units contained in the specific polyamide resin, 70 mol % or more of the dicarboxylic acid-derived constituent units are derived from an α,ω-linear aliphatic dicarboxylic acid having from 8 to 12 carbon atoms, preferably 75 mol % or more, more preferably 80 mol % or more, further more preferably 85 mol % or more, even more preferably 90 mol % or more, still more preferably 95 mol % or more, and yet even more preferably 99 mol % or more are derived from an α,ω-linear aliphatic dicarboxylic acid having from 8 to 12 carbon atoms.

The α,ω-linear aliphatic dicarboxylic acid having from 8 to 12 carbon atoms is exemplified by suberic acid, azelaic acid, sebacic acid, 1,9-nonanedicarboxylic acid, and dodecanedioic acid, and is preferably sebacic acid, 1,9-nonanedicarboxylic acid, and dodecanedioic acid, and more preferably sebacic acid and dodecanedioic acid.

Among the dicarboxylic acids constituting the dicarboxylic acid-derived constituent unit that can be contained in the specific polyamide resin, the dicarboxylic acid other than the α,ω-linear aliphatic dicarboxylic acid having from 8 to 12 carbon atoms is exemplified by α,ω-linear aliphatic dicarboxylic acids having 7 or less carbon atoms, alicyclic dicarboxylic acids, and aromatic dicarboxylic acids.

The α,ω-linear aliphatic dicarboxylic acid having from 7 or less carbon atoms is exemplified by succinic acid, glutaric acid, adipic acid, and pimelic acid, and is preferably adipic acid.

The alicyclic dicarboxylic acid is exemplified by 4,4'-methylenebis(2-methylcyclohexane-1-carboxylic acid), 4,4'-methylenebis(cyclohexane-1-carboxylic acid), 4,4'-methylenebis(2-methylcyclohexane-1-carboxylic acid), 4,4'-oxobis(cyclohexane-1-carboxylic acid), and 4,4'-thiobis(cyclohexane-1-carboxylic acid).

The aromatic dicarboxylic acid is exemplified by terephthalic acid, isophthalic acid, 1,3-naphthalenedicarboxylic acid, 1,4-naphthalenedicarboxylic acid, 1,8-naphthalenedicarboxylic acid, and 2,6-naphthalenedicarboxylic acid, and is preferably at least one of isophthalic acid, 1,3-naphthalenedicarboxylic acid, 1,4-naphthalenedicarboxylic acid, 1,8-naphthalenedicarboxylic acid, or 2,6-naphthalenedicarboxylic acid, more preferably at least one of isophthalic acid or 2,6-naphthalenedicarboxylic acid, and even more preferably isophthalic acid.

The specific polyamide resin is constituted of the dicarboxylic acid-derived constituent unit and the diamine-derived constituent unit but may also contains a constituent unit other than the dicarboxylic acid-derived constituent unit and the diamine-derived constituent unit, or any other moiety, such as a terminal group. The constituent unit other than the dicarboxylic acid-derived constituent unit and the diamine-derived constituent unit can be exemplified by, but not limited to, constituent units derived from lactams, such as ε-caprolactam, valerolactam, laurolactam, and undecalactam; and from aminocarboxylic acids, such as 11-aminoundecanoic acid and 12-aminododecanoic acid. Furthermore, the specific polyamide resin may contain a minor component, such as an additive used in synthesis.

Of the specific polyamide resin used in the present invention, preferably 70 mass % or more, more preferably 80 mass % or more, even more preferably 90 mass % or more, and still more preferably 95 mass % or more are dicarboxylic acid-derived constituent units and the diamine-derived constituent units.

A preferred embodiment of the specific polyamide resin is a polyamide resin constituted of the diamine-derived constituent units and the dicarboxylic acid-derived constituent units, in which 70 mol % or more (preferably 75 mol % or more, more preferably 80 mol % or more, even more preferably 85 mol % or more, still more preferably 90 mol % or more, yet even more preferably 95 mol % or more, and even still more preferably 99 mol % or more) of the diamine-derived constituent units are derived from the compound represented by Formula (2), and 70 mol % or more (preferably 75 mol % or more, more preferably 80 mol % or more, even more preferably 85 mol % or more, still more preferably 90 mol % or more, yet even more preferably 95 mol % or more, and even still more preferably 99 mol % or more) of the dicarboxylic acid-derived constituent units are derived from at least one of sebacic acid and dodecanedioic acid.

A more preferred embodiment of the specific polyamide resin is a polyamide resin constituted of the diamine-derived constituent units and the dicarboxylic acid-derived constituent units, in which 70 mol % or more (preferably 75 mol % or more, more preferably 80 mol % or more, even more preferably 85 mol % or more, still more preferably 90 mol % or more, yet even more preferably 95 mol % or more, and even still more preferably 99 mol % or more) of the diamine-derived constituent units are derived from at least one selected from the group consisting of 4,4'-methylenebis (2-methylcyclohexane-1-amine) and 4,4'-methylenebis(cyclohexane-1-amine), and 70 mol % or more (preferably 75 mol % or more, more preferably 80 mol % or more, even more preferably 85 mol % or more, still more preferably 90 mol % or more, yet even more preferably 95 mol % or more, and even still more preferably 99 mol % or more) of the dicarboxylic acid-derived constituent units are derived from at least one of sebacic acid and dodecanedioic acid.

The specific polyamide resin is preferably produced by a melt polycondensation (melt polymerization) method using a phosphorus atom-containing compound as a catalyst. The melt polycondensation method is preferably a method of adding a raw material diamine dropwise to a molten raw material dicarboxylic acid and increasing the temperature under pressure to carry out polymerization while removing condensed water, or a method of increasing the temperature of a salt formed from a raw material diamine and a raw material dicarboxylic acid under pressure conditions in the presence of water to carry out polymerization in the molten state while removing added water and condensed water.

The specific polyamide resin is typically an amorphous polyamide resin. The amorphous polyamide resin in the present specification is a resin having a crystal melting enthalpy ΔHm of less than 10 J/g and is meant to include what is called microcrystalline polyamide resins. The crystal melting enthalpy ΔHm of the amorphous polyamide resin in the present specification is preferably 5 J/g or less and more preferably 3 J/g or less. The crystal melting enthalpy is measured according to the method described in Examples below.

The lower limit of the number average molecular weight of the specific polyamide resin is preferably 8000 or higher and more preferably 10000 or higher. The upper limit of the number average molecular weight is preferably 25000 or lower and more preferably 20000 or lower.

The number average molecular weight can be measured by the following method.

An amount of 0.3 g of the polyamide resin is added to a mixed solvent of phenol/ethanol in a volume ratio of 4/1, and the mixture is stirred at 25° C. to completely dissolve the polyamide resin. Then, the inner wall of the vessel is rinsed with 5 mL of methanol under stirring, and the terminal amino group concentration [NH$_2$] is determined by neutralization titration with a 0.01 mol/L hydrochloric acid aqueous solution. An amount of 0.3 g of the polyamide resin is added to benzyl alcohol, and the mixture is stirred at 170° C. under a nitrogen stream to completely dissolve the polyamide resin. Then, the mixture is cooled to 80° C. or lower under a nitrogen stream, the inner wall of the vessel is rinsed with 10 mL of methanol under stirring, and the terminal carboxyl group concentration [COOH] is determined by neutralization titration with a 0.01 mol/L sodium hydroxide aqueous solution. The number average molecular weight is determined from the measured terminal amino group concentration [NH$_2$] (unit: μeq/g) and the measured terminal carboxyl group concentration [COOH] (unit: μeq/g) by the following equation.

Number average molecular weight (Mn)=2000000/([COOH]+[NH$_2$])

The specific polyamide resin has a relative viscosity of preferably 3.00 or lower, more preferably 2.80 or lower, and even more preferably 2.60 or lower when the relative viscosity is measured according to JIS K 6810 by dissolving the sample in a 96% sulfuric acid to give a concentration of 0.01 g/mL and using an Ostwald viscometer at 25° C. In addition, the lower limit of the relative viscosity is preferably 1.60 or higher, more preferably 1.80 or higher, and even more preferably 1.90 or higher.

The specific polyamide resin has a glass transition temperature of preferably 100° C. or higher, more preferably 110° C. or higher, and even more preferably 120° C. or higher. The upper limit of the glass transition temperature is not particularly specified but is, for example, preferably 220° C. or lower or may be 180° C., and the upper limit of 170° C. or lower is also sufficiently at a practical level.

The method for measuring the glass transition temperature follows the method described in Examples below.

The lower limit of the content of the specific polyamide resin in the resin composition of the present invention is preferably 50 mass % or more and may be 80 mass % or more or 95 mass % or more. In addition, the upper limit of the content of the specific polyamide resin in the resin composition of the present invention is preferably 99.9 mass % or less.

The resin composition of the present invention may contain only one, or two or more types of specific polyamide resins. When two or more types of specific polyamide resins are contained, the total amount is in the above range.

Compound Represented by Formula (1)

The resin composition of the present invention contains the compound represented by Formula (1) in a range of 3 to 100 mass ppm of the resin composition. The resin composition can have an improved color tone due to its content of the compound represented by Formula (1) of 3 mass ppm or more and can effectively prevent mold fouling and the like due to the content of 100 mass ppm or less.

Formula (1)

[Chem. 8]

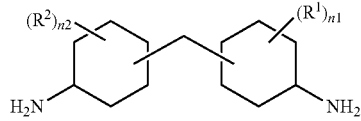

where $R^1$ and $R^2$ each independently represent an alkyl group having from 1 to 4 carbon atoms, and n1 and n2 are each independently an integer from 0 to 4.

The details of the compound represented by Formula (1) are synonymous with those described for the specific polyamide resin, and the preferred ranges are also the same.

In the resin composition of the present invention, 60 mol % or more (preferably 80 mol % or more, more preferably 90 mol % or more, and even more preferably 95 mol % or more) of the diamines constituting the specific polyamide resin have the same structure as that of the compound represented by Formula (1) contained in the resin composition. When two or more diamines constitute the polyamide resin, and/or when two or more compounds represented by Formula (1) are contained in the resin composition, 50 mol % or more (preferably 60 mol % or more and more preferably 70 mol % or more) of the composition are preferably the same.

The content of the compound represented by Formula (1) in the resin composition of the present invention is preferably more than 3 mass ppm, more preferably 3.5 mass ppm, and even more preferably 5 mass ppm or more, and may be 10 mass ppm or more, 15 mass ppm or more, 18 mass ppm or more, or 20 mass ppm or more. The content is preferably 98 mass ppm or less, more preferably less than 95 mass ppm, even more preferably 80 mass ppm or less, still more preferably 70 mass ppm or less, yet even more preferably 65 mass ppm or less, and even still more preferably 60 mass ppm or less, and may be 55 mass ppm or less or 40 mass ppm or less.

The resin composition of the present invention may contain only one, or two or more compounds represented by Formula (1). When two or more compounds are contained, the total amount is in the above range.

A known technique can be used as the method for adding the compound represented by Formula (1) in the resin composition of the present invention. For example, the compound represented by Formula (1) may be dry blended to pellets of the specific polyamide resin prepared in advance, and the blend as is may be injection-molded or extrusion-molded to directly form a molded product formed from the resin composition of the present invention; or the compound represented by Formula (1) may be melt-kneaded with the specific polyamide resin that has been turned into a molten state using a single-screw extruder, a twin-screw extruder, or the like, strands extruded from a strand die may be cooled and pelletized to obtain pellets formed from the resin composition of the present invention, and the pellets may be injection-molded or extrusion-molded to form a molded product. Furthermore, the compound represented by Formula (1) may be added to a reaction vessel in which a polymerization reaction of the specific polyamide resin has been performed, the polymer may be extruded as strands and pelletized to obtain pellets formed from the resin composition of the present invention.

Additional Component

The resin composition of the present invention may consist of only the specific polyamide resin and the compound represented by Formula (1) or may contain an additional component.

As an additional component, a polyamide resin other than the specific polyamide resin; a thermoplastic resin other than the polyamide resin; or an additive, such as an antioxidant, a filler, a matting agent, a heat resistant stabilizer, a weather resistant stabilizer, an ultraviolet absorber, a plasticizer, a flame retardant, an antistatic agent, a coloration inhibitor, an anti-gelling agent, an impact modifier, a lubricant, a colorant, and a conductive additive, can be added as necessary. One, or two or more of these additives each may be used.

The total amount of these is preferably 10 mass % or less and more preferably 5 mass % or less and may be 3 mass % or less or 1 mass % or less of the resin composition. In addition, the lower limit may be 0.1 mass % or more.

Antioxidant

The compound represented by Formula (1) serves as an antioxidant, thus the resin composition of the present invention does not need to contain an antioxidant but may contain an additional antioxidant.

The additional antioxidant is not particularly limited and is to be appropriately selected from known agents referred to as an antioxidant or a thermal stabilizer.

The additional antioxidant is exemplified by phenol-based antioxidants, phosphorus-based antioxidants, hindered amine-based antioxidants, aromatic amine-based antioxidants, sulfur-based antioxidants, and imidazole-based antioxidants, and the resin composition preferably contains at least one selected from the group consisting of phenol-based antioxidants and phosphorus-based antioxidants, and more preferably contains at least a phenol-based antioxidant.

One additional antioxidant may be used alone, or two or more in combination. When two or more additional antioxidants are used in combination, a combination of a phenol-based antioxidant and another antioxidant is preferred, and a combination of a phenol-based antioxidant and a phosphorus-based antioxidant is more preferred.

Specific examples of the additional antioxidant can be considered with reference to descriptions in paragraphs 0051 to 0058 in JP 2018-180381 A, descriptions in paragraphs 0023 to 0027 in JP 2018-178124 A, descriptions in paragraphs 0144 to 0147 in JP 2018-178095 A, descriptions in paragraph 0080 of JP 2018-178026 A, descriptions in paragraph 0046 in JP 2018-177996 A, descriptions in paragraphs 0028 to 0030 in JP 2018-043773 A, and descriptions in paragraphs 0049 to 0055 in JP 2014-148560 A, the contents of which are incorporated in the present specification.

The content of the additional antioxidant when contained is preferably 0.001 mass % or more and more preferably 0.01 mass % or more of the resin composition. In addition, the upper limit of the content is preferably 1 mass % or less and more preferably 0.5 mass % or less. As described above, only one, or two or more antioxidants may be used, but when two or more antioxidants are used, the total amount is preferably in the above range.

In addition, the resin composition of the present invention can be configured to contain substantially no additional antioxidant. "To contain substantially no" means that the content is less than 0.001 mass % of the resin composition.

Additional Thermoplastic Resin

The polyamide resin other than the specific polyamide resin may be either an amorphous polyamide resin or a crystalline polyamide resin. Specifically, such a polyamide resin is exemplified by polyamide 6, polyamide 66, polyamide 46, polyamide 6/66 (a copolymer aimed from a polyamide 6 component and a polyamide 66 component), polyamide 610, polyamide 612, polyamide 11, polyamide 12, MXD6 (poly(m-xylylene adipamide)), MPXD6 (poly(m-, p-xylylene adipamide)), MXD10 (poly(m-xylylene sebacamide)), MPXD10 (poly(m-, p-xylylene sebacamide)), PXD10 (poly(p-xylylene sebacamide)), MXD6I, 6T/6I, and 9T. One, or two or more of these additional polyamide resins each may be used.

When the resin composition of the present invention contains a polyamide resin other than the specific polyamide resin, the content of the polyamide resin other than the specific polyamide resin is preferably 30 mass % or less, more preferably from 1 to 30 mass %, and even more preferably from 1 to 10 mass % of the resin component contained in the resin composition of the present invention. In addition, the resin composition of the present invention may be configured to contain substantially no polyamide resin other than the specific polyamide resin. "To contain substantially no polyamide resin other than the specific polyamide resin" means that the content of the polyamide resin other than the specific polyamide resin is less than 1 mass % of the resin component contained in the resin composition of the present invention.

The thermoplastic resin other than the polyamide resin can be exemplified by polyester resins, such as polyethylene terephthalate, polybutylene terephthalate, polyethylene naphthalate, and polybutylene naphthalate; and polyolefin resins, such as polypropylene (PP), cycloolefin polymers (COP), and cycloolefin copolymers (COC). One, or two or more of these thermoplastic resins other than the polyamide resin each may be used.

When the resin composition of the present invention contains a thermoplastic resin other than the polyamide resin, the content of the thermoplastic resin other than the polyamide resin is preferably 10 mass % or less and more preferably from 1 to 10 mass % of the resin component contained in the resin composition of the present invention. In addition, the resin composition of the present invention may be configured to contain substantially no thermoplastic resin other than the polyamide resin. "To contain substantially no thermoplastic resin other than the polyamide resin" means that the content of the thermoplastic resin other than the polyamide resin is less than 1 mass % of the resin component contained in the resin composition of the present invention.

The resin composition of the present invention when molded into a 4-mm thick test piece has a Yi (yellow index) value of preferably 1.00 or lower, more preferably 0.70 or lower, even more preferably 0.50 or lower, and still more preferably 0.40 or lower. The lower limit of the YI value is desirably 0 or higher, but the lower limit of, for example, 0.10 or higher is also at a practical level.

Applications

The present invention also discloses a molded product formed from the resin composition of the present invention. The molded product formed from the resin composition of the present invention is exemplified by injection molded products, thin-walled molded products, hollow molded products, films (including sheets), extrusion molded products, fibers, hoses, and tubes.

The resin composition of the present invention can be molded by a known molding method, such as injection molding, blow molding, extrusion molding, compression molding, stretching, and vacuum molding. That is, the present invention relates to a method for producing a molded product, the method including molding the resin composition of the present invention.

The molded product formed from the resin composition of the present invention contains the specific polyamide resin and the compound represented by Formula (1), and the content of the compound represented by Formula (1) in the molded product is preferably from 3 to 100 mass ppm in the molded product. However, in the molded product formed from the resin composition of the present invention, the compound represented by Formula (1) may be decomposed or volatilized by heating during molding or the like. Thus, a molded product with a content of the compound represented by Formula (1) of less than 3 mass ppm in the molded product is also included within the scope of the present invention as long as the compound represented by Formula (1) is contained in a proportion of 3 to 100 mass ppm in the raw material resin composition.

In addition, the molded product of the present invention may be a component, a part, or the like, and it goes without saying that such a component or part is to contain the compound represented by Formula (1) in the above content.

Examples of fields of use of molded products formed from the resin composition of the present invention include transportation equipment components for automobiles, etc.; general mechanical components; precision mechanical components; electronic and electrical equipment components; OA equipment parts; building materials and housing related components; medical devices; optical products; industrial materials; leisure sporting goods; amusement equipment; medical products; daily necessities, such as food packaging films; and defense and aerospace products.

An example of embodiments of the molded product of the present invention is exemplified by filter balls, filters, switch sensors, other sensors, housing for electronic and electrical components, lenses, transparent films, sunglasses, medical eyeglasses, medical equipment covers, breathing masks, transfusion bags, other medical supplies, sundries, containers, daily necessities, automotive interior materials, automobile covers, sedimenters, site glasses, and other injection molded bodies.

In addition, the resin composition of the present invention can be blended as a polyamide resin component in various resin compositions.

Furthermore, another example of an embodiment of the molded product formed from the resin composition of the present invention includes a monolayer or multilayer container including a layer foil led from the resin composition of the present invention. The multilayer container is exemplified by a multilayer container having a layer formed from a composition containing a polyolefin resin, a layer formed from the resin composition of the present invention, and a layer formed from a composition containing a polyolefin resin in this order. The polyolefin resin is exemplified by polypropylene (PP), cycloolefin polymers (COP), and cycloolefin copolymers (COC). Moreover, the multilayer container may have an adhesive layer between the layer formed from the composition containing a polyolefin resin and the layer formed from the resin composition of the present invention. Such multilayer containers can be preferably used as food or pharmaceutical containers. The pharmaceutical containers are exemplified by ampoules, vials, vacuum blood collection tubes, and prefilled syringes.

The present invention also discloses an antioxidant for polyamide resins, the antioxidant containing a compound represented by Formula (1). Such an antioxidant also has an advantage of having excellent compatibility with polyamide resins.

The antioxidant of the present invention is preferably used as an antioxidant for a polyamide resin having a constituent unit derived from a compound represented by Formula (1) and is more preferably used as an antioxidant of the specific polyamide resin. In addition, 80 mol % or more (preferably 90 mol % or more and more preferably 95 mol % or more) of the diamine(s) constituting the polyamide resin in which the antioxidant of the present invention is used preferably has/have the same structure as that of the antioxidant of the present invention. When two or more diamines constitute the polyamide resin, and/or when two or more compounds represented by Formula (1) are contained in the antioxidant, 80 mol % or more (preferably 90 mol % or more and more preferably 95 mol % or more) of the composition are preferably the same.

EXAMPLES

The present invention will be described in more detail below through examples. The following materials, usage amounts, proportions, processing details, processing procedures, and the like described in the examples may be changed, as appropriate, as long as there is no deviation from the spirit of the present invention. Therefore, the scope of the present invention is not limited to the specific examples described below.

Synthesis Examples

Synthesis of MACM12

A polyamide resin (MACM12) was synthesized from 4,4'-methylenebis(2-methylcyclohexane-1-amine) (MACM manufactured by Xiamen Grandachem Co., Ltd.) and dodecanedioic acid (available from Laiyang Himount Bio-Products Technology Co., Ltd.).

Specifically, precisely weighed 9500 g (40.9 mol) of dodecanedioic acid (available from Kanto Chemical Co., Inc.), 1.53 g (0.0144 mol) of sodium hypophosphite (available from Kanto Chemical Co., Inc.), and 1.06 g (0.0130 mol) of sodium acetate (available from Kanto Chemical Co., Ltd.) were placed in a pressure-resistant reaction vessel having an internal volume of 50 L and equipped with a stirrer, a partial condenser, a total condenser, a pressure regulator, a thermometer, a dropping funnel and a pump, an aspirator, a nitrogen inlet tube, a bottom drain valve, and a strand die. The reaction vessel was thoroughly purged with nitrogen and then sealed, and the temperature was increased to 180° C. under stirring while the pressure in the vessel was maintained at 0.4 MPa. After the temperature reached 180° C., the MACM stored in the dropping funnel was started to be added dropwise to the raw material in the reaction vessel, and the temperature in the reaction vessel was increased to 250° C. while condensed water being produced was being removed out of the system and the pressure in the reaction vessel was maintained at 0.4 MPa. After completing the dropwise addition of 4,4'-methylenebis(2-methylcyclohexane-1-amine), the pressure in the reaction vessel was gradually returned to normal pressure while the temperature was gradually increased to 290° C. Then, the pressure in the reaction vessel was reduced to 80 kPa using the aspirator, and the condensed water was removed. Stirring torque of the stirrer was observed under a reduced pressure, and stirring was terminated when a predetermined torque was reached. Then, the inside of the reaction vessel was pressurized with nitrogen, the bottom drain valve was opened, and the polymer was extruded from the strand die to form strands. Then, the strands were cooled, pelletized using a pelletizer, and a polyamide resin in pellet form was obtained. The resulting pellets were immersed in water at 60° C. for 140 hours. The amount of 4,4'-methylenebis(2-methylcyclohexane-1-amine) in the resulting pellets was 2 mass ppm.

In addition, the MACM12 had a crystal melting enthalpy ΔHm of 3 J/g or lower in the temperature increasing process.

Furthermore, the glass transition temperature (Tg) of the MACM12 was 156° C.

Synthesis of PACM12

A polyamide resin (PACM12) was obtained by changing 4,4'-methylenebis(2-methylcyclohexane-1-amine) in the synthesis of MACM12 above to an equimolar amount of 4,4'-methylenebis(cyclohexane-1-amine) (PACM manufactured by BASF) and similarly performing other procedures. The amount of 4,4'-methylenebis (cyclohexane-1-amine) in the resulting pellets was 2 mass ppm.

In addition, the PACM12 was found to have a crystal melting enthalpy ΔHm of about 7.5 J/g in the temperature increasing process and to be an amorphous polyamide resin.

Furthermore, the glass transition temperature (Tg) of the PACM12 was 130° C.

Synthesis of MACM10

A polyamide resin (MACM10) was obtained by changing dodecanedioic acid in the synthesis of MACM12 above to an equimolar amount of sebacic acid (SA, Casda Biomaterials Co., Ltd.) and similarly performing other procedures. The amount of 4,4'-methylenebis(2-methylcyclohexane-1-amine) in the resulting pellets was 2 mass ppm.

In addition, the MACM10 had a crystal melting enthalpy ΔHm of 3 J/g or lower in the temperature increasing process.

Furthermore, the glass transition temperature (Tg) of the MACM10 was 146° C.

Measurements of Glass Transition Temperature (Tg) and Crystal Melting Enthalpy ΔHm For the glass transition temperature, a value obtained by heating a sample (each polyamide resin synthesized above) from room temperature to 300° C. at a temperature increase rate of 10° C./min in a nitrogen stream using a differential scanning calorimeter (DSC). The melting enthalpy was measured by heating a sample from room temperature to 300° C. at a temperature increase rate of 10° C./min, then immediately cooling the sample to not higher than room temperature, and heating the sample again from room temperature to 250° C. at a temperature increase rate of 10° C./min.

In the present example, DSC-60 available from Shimadzu Corporation was used as the differential scanning calorimeter.

In addition, the crystal melting enthalpy ΔHm of the polyamide resin in the temperature increasing process was measured in accordance with JIS K 7121 and K 7122.

Production Examples 1 to 9

To each of the polyamide resins shown in Table 1 among the polyamide resins synthesized as described above, diamines shown in Table 1 were each added so that the content of the diamine in the pellets finally obtained was as shown in Table 1. Mixtures were each melt-kneaded using a twin screw extruder (TEM37BS available from Toshiba Machine Co., Ltd.) and a screw provided with a kneading zone at a cylinder temperature of 300° C. Strands extruded through a strand die were cooled and pelletized, and resin compositions 1 to 9 were obtained.

Of these, for the resin composition 7, which was used in Comparative Example 1 described below, no diamine was added to the polyamide resin, and the polyamide resin as is was melt-kneaded under the same conditions.

The compound represented by Formula (1) in the resin composition (pellets) obtained above was quantified using a gas chromatograph (GC).

An amount of 0.3 g of each resin composition (pellets) was weighed and dissolved in 6.4 g of 1,3-hexafluoropropanediol (HFIP), and then the resin component was re-precipitated with 15.1 g of dimethylformamide (DMF). 1-decanol was added as an internal standard, and the supernatant was used as a post-filtration gas chromatography sample. The calibration curve was prepared using solutions of the diamine (the compound represented by Formula (1)) in HFIP/DMF adjusted to 20 mass ppm, 50 mass ppm, 100 mass ppm, and 1200 mass ppm.

That is, calibration curves were created using 4,4'-methylenebis(2-methylcyclohexane-1-amine) in Examples 1 to 4, and 6, and Comparative Examples 1 to 3, and using solutions of 4,4'-methylenebis(cyclohexane-1-amine) in HFIP/DMF in Example 5.

A gas chromatograph (7890B) available from Agilent Technologies was used as the gas chromatograph.

Examples 1 to 6 and Comparative Examples 1 to 3

Test pieces (injection molded products) in 4 mm×100 mm×100 mm were prepared using each resin composition (pellets) obtained in the above production examples and using an injection molding machine (SE130DU-HP available from Sumitomo Heavy Industries, Ltd.) at a cylinder temperature of 300° C. and a residence time of 30 seconds.

YI (yellow index) values of the resulting test pieces were measured in accordance with JIS K 7373.

The YI values were measured using a color turbidity meter (product name: "COH-300A", available from Nippon Denshoku Industries Co., Ltd.).

The YI values were evaluated by classifying as follows.
A: 0 or higher and 0.40 or lower
B: higher than 0.40 and 0.70 or lower
C: higher than 0.70

In addition, in the injection molding, the mold was cooled, and then the number of shots until fouling was visually observed was measured. Specifically, a first shot after starting the molding was counted as one shot, and the number of shots until fouling of the mold was observed was measured. When molding with continuous 10000 shots or more caused no fouling of the mold, the result is indicated as ">10000".

TABLE 1

|  | Example 1 | Example 2 | Example 3 | Example 4 | Example 5 | Example 6 | Comparative Example 1 | Comparative Example 2 | Comparative Example 3 |
|---|---|---|---|---|---|---|---|---|---|
| Resin composition | Resin composition 1 | Resin composition 2 | Resin composition 3 | Resin composition 4 | Resin composition 5 | Resin composition 6 | Resin composition 7 | Resin composition 8 | Resin composition 9 |
| Polyamide resin | MACM12 | MACM12 | MACM12 | MACM12 | PACM12 | MACM10 | MACM12 | MACM12 | MACM12 |
| Added diamine | MACM | MACM | MACM | MACM | PACM | MACM | MACM | MACM | MACM |
| Diamine amount in resin composition | 4 ppm | 20 ppm | 50 ppm | 95 ppm | 30 ppm | 60 ppm | 2 ppm | 110 ppm | 150 ppm |
| Color tone | B | A | A | A | A | A | C | A | A |
| Number of times of shots until mold fouling appeared | >10000 | >10000 | >10000 | >5000 | >10000 | >10000 | >10000 | 1000 | 200 |

In the above table, the unit of the diamine amount in the pellets is mass ppm. In addition, the unit of the number of shots until mold fouling occurred is shots.

As is clear from the above results, the resin compositions with the diamine amount of 3 to 100 mass ppm provided injection-molded products with an excellent color tone and were less likely to cause mold fouling (Examples 1 to 6).

On the other hand, the resin composition with the diamine amount of less than 3 mass ppm (Comparative Example 1) resulted in an injection-molded product with a poor color tone. In addition, the resin compositions with the diamine amount of more than 100 mass ppm (Comparative Examples 2 and 3) caused mold fouling at extremely small number of shots.

The invention claimed is:

1. A resin composition comprising:
a polyamide resin and 3-100 mass ppm of a compound represented by Formula (1) based on the total weight of the resin composition,
wherein the polyamide resin constituted of diamine-derived constituent units and dicarboxylic acid-derived constituent units,
70 mol % or more of the diamine-derived constituent units being derived from the compound represented by Formula (1), and
70 mol % or more of the dicarboxylic acid-derived constituent units being derived from an α,ω-linear aliphatic dicarboxylic acid having from 8 to 12 carbon atoms, Formula (1)

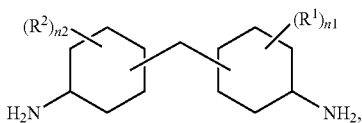

where $R^1$ and $R^2$ each independently represent an alkyl group having from 1 to 4 carbon atoms, and n1 and n2 are each independently an integer from 0 to 4.

2. The resin composition according to claim 1, wherein the compound represented by Formula (1) is represented by Formula (2):

Formula (2)

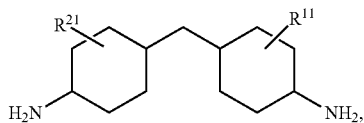

where $R^{11}$ and $R^{21}$ each independently represent a hydrogen atom or an alkyl group having from 1 to 4 carbon atoms.

3. The resin composition according to claim 1, wherein the compound represented by Formula (1) is at least one selected from the group consisting of 4,4'-methylenebis(2-methylcyclohexane-1-amine) and 4,4'-methylenebis(cyclohexane-1-amine).

4. The resin composition according to claim 1, wherein 70 mol % or more of the dicarboxylic acid-derived constituent units are constituent units derived from at least one of sebacic acid and dodecanedioic acid.

5. The resin composition according to claim 1, wherein the polyamide resin is an amorphous polyamide resin.

6. The resin composition according to claim 1, wherein 95 mass % or more of the resin composition is the polyamide resin.

7. The resin composition according to claim 1, wherein the content of the compound represented by Formula (1) is from 18 to 70 mass ppm of the resin composition.

8. The resin composition according to claim 2, wherein 70 mol % or more of the dicarboxylic acid-derived constituent units are constituent units derived from at least one of sebacic acid and dodecanedioic acid.

9. The resin composition according to claim 2, wherein the polyamide resin is an amorphous polyamide resin.

10. The resin composition according to claim 2, wherein 95 mass % or more of the resin composition is the polyamide resin.

11. The resin composition according to claim 2, wherein the content of the compound represented by Formula (1) is from 18 to 70 mass ppm of the resin composition.

12. The resin composition according to claim 3, wherein 70 mol % or more of the dicarboxylic acid-derived constituent units are constituent units derived from at least one of sebacic acid and dodecanedioic acid.

13. The resin composition according to claim 3, wherein the polyamide resin is an amorphous polyamide resin.

14. The resin composition according to claim 3, wherein 95 mass % or more of the resin composition is the polyamide resin.

15. The resin composition according to claim 3, wherein the content of the compound represented by Formula (1) is from 18 to 70 mass ppm of the resin composition.

16. The resin composition according to claim 4, wherein the polyamide resin is an amorphous polyamide resin.

17. The resin composition according to claim 4, wherein 95 mass % or more of the resin composition is the polyamide resin.

18. A molded product formed from the resin composition described in claim 1.

19. A method for producing a molded product, the method comprising molding the resin composition described in claim 1.

* * * * *